(12) United States Patent
Lear et al.

(10) Patent No.: US 8,455,844 B2
(45) Date of Patent: Jun. 4, 2013

(54) SYSTEM AND METHOD FOR TIME-DIVISION MULTIPLEXED OPTICAL SENSING OF BIOSENSORS

(75) Inventors: Kevin L. Lear, Fort Collins, CO (US); Sean B. Pieper, Lincoln, NE (US)

(73) Assignee: Colorado State University Research Foundation, Fort Collins, CO (US)

( * ) Notice: Subject to any disclaimer, the term of this patent is extended or adjusted under 35 U.S.C. 154(b) by 303 days.

(21) Appl. No.: 12/722,446

(22) Filed: Mar. 11, 2010

(65) Prior Publication Data

US 2010/0230614 A1  Sep. 16, 2010

Related U.S. Application Data

(60) Provisional application No. 61/159,361, filed on Mar. 11, 2009.

(51) Int. Cl.
*G01N 21/64* (2006.01)

(52) U.S. Cl.
USPC ...................................................... 250/458.1

(58) Field of Classification Search
CPC ...................................................... G01N 21/64
USPC ...................................................... 250/458.1
See application file for complete search history.

(56) References Cited

U.S. PATENT DOCUMENTS

| | | | |
|---|---|---|---|
| 4,848,906 A | | 7/1989 | Layton |
| 5,140,609 A | * | 8/1992 | Jensen et al. .................. 374/101 |
| 5,462,879 A | * | 10/1995 | Bentsen .......................... 436/136 |
| 5,866,321 A | * | 2/1999 | Matsue et al. ..................... 435/5 |
| 6,437,345 B1 | | 8/2002 | Bruno-Raimondi et al. |
| 7,381,538 B2 | | 6/2008 | Reardon et al. |
| 7,709,249 B2 | * | 5/2010 | Bedingham et al. ........ 435/288.7 |
| 2009/0026092 A1 | | 1/2009 | Reardon et al. |
| 2009/0078886 A1 | * | 3/2009 | Schutzmann et al. ..... 250/459.1 |
| 2009/0221014 A1 | | 9/2009 | Reardon et al. |

FOREIGN PATENT DOCUMENTS

| | | |
|---|---|---|
| EP | 277699 A2 | 8/1988 |
| EP | 1078248 A1 | 2/2001 |
| WO | WO99/58963 | 11/1999 |
| WO | WO03/025627 | 3/2003 |
| WO | WO/2009/126841 | 10/2009 |

OTHER PUBLICATIONS

Al-Raweshidy, H.S., et al. "Electro-optic correlation in a spread spectrum multiplexing system for fibre optic interferometers", Optics Communications 81 Feb. 15, 1991, pp. 171-174.
Lipson, D. et al., Multifiber, Multiwavelength, Fiber Optic Fluorescence Spectrophotometer, IEEE Trans. Biomed. Eng. vol. 39, No. 9 Sep. 1992, pp. 886-892.

* cited by examiner

*Primary Examiner* — Constantine Hannaher
(74) *Attorney, Agent, or Firm* — Lathrop & Gage, LLP

(57) ABSTRACT

A measurement system for use with fluorescent chemosensors has multiple stimulus light sources each coupled to at least one sensor. Multiple sensors each receiving light from a different light source connect to each of one or more photodetectors. A processing device drives the light sources in a time-division multiplexed manner, and reads the photodetector at an appropriate time for each sensor. The processing device calibrates the sensor readings and provides them in a way that is identified to the associated sensor.

26 Claims, 3 Drawing Sheets

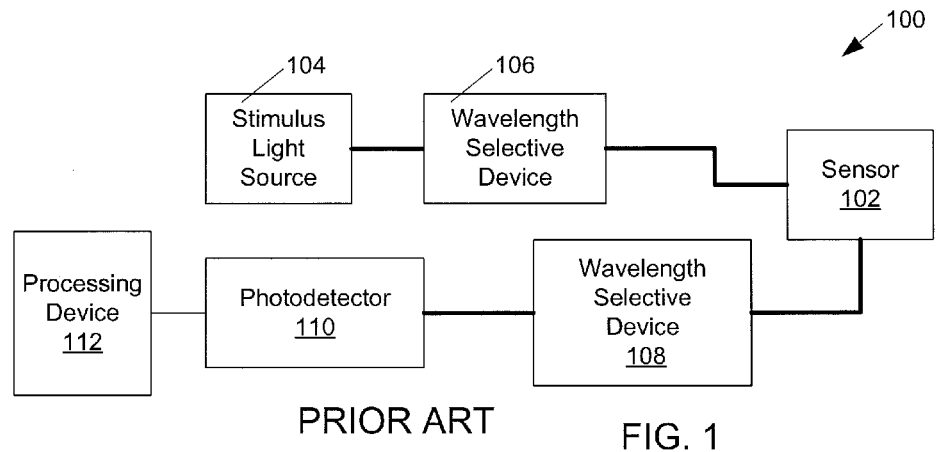
PRIOR ART        FIG. 1
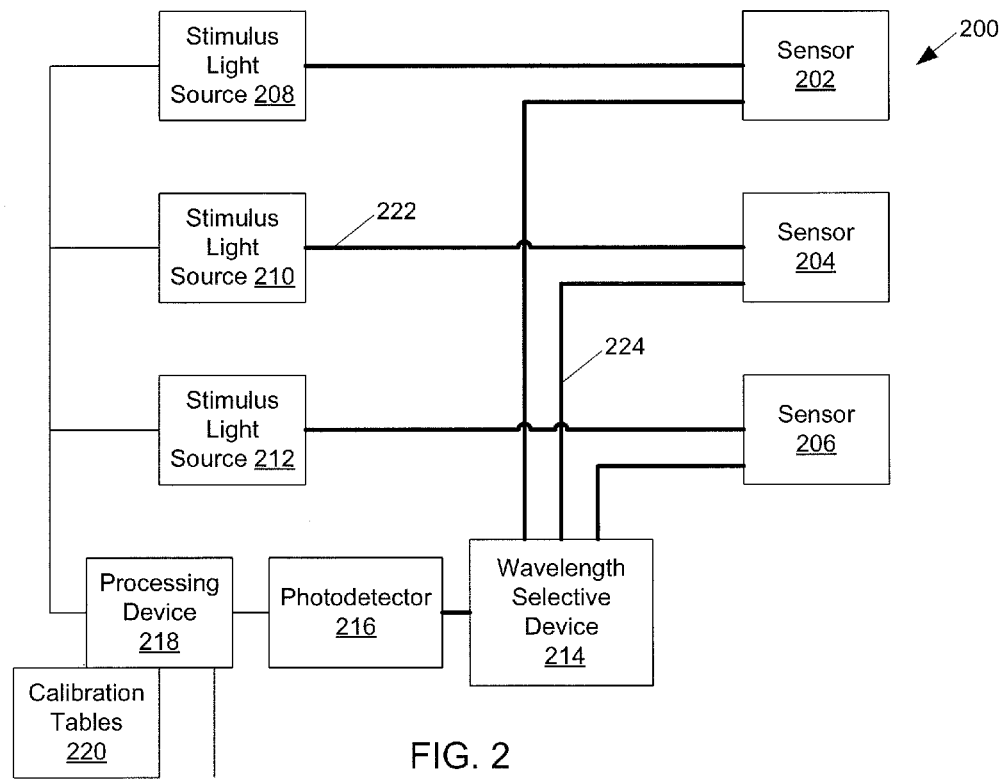
FIG. 2

SYSTEM AND METHOD FOR TIME-DIVISION MULTIPLEXED OPTICAL SENSING OF BIOSENSORS

CROSS-REFERENCE TO RELATED APPLICATIONS

The present application claims priority from U.S. Provisional Patent Application No. 61/159,361, filed 11 Mar. 2009, which is incorporated herein by reference.

GOVERNMENT RIGHTS CLAUSE

This invention was made with government support under Grant No. BES0529048 awarded by the National Science Foundation. The government has certain rights in the invention.

BACKGROUND

There are many new chemo-optical sensing devices that are read optically.

Many of these sensors involve a chemosensor component that is photometrically interrogated by an electro-optical component. In these sensors, the electro-optical component may measure optical changes at the chemosensor component such as absorption changes at ultraviolet and/or visible wavelengths (e.g. color changes), fluorescent and/or phosphorescent emissions, and optical scattering properties. When fluorescent reagents are utilized a fluorescent substance is excited by stimulus light at a stimulus wavelength, and one or more substances in the chemosensor component absorbs this stimulus light and emits light of a longer wavelength.

Such sensors may have enzymatic components in their chemosensor component, such as the enzymatic biosensors described in U.S. patent application Ser. No. 12/358,140, hereinafter the '140 application, filed 22 Jan. 2009, and entitled ENZYMATIC BIOSENSORS WITH ENHANCED ACTIVITY RETENTION FOR DETECTION OF ORGANIC COMPOUNDS, which is hereby incorporated herein by reference.

For example, photoluminescence (PL), a generic term for both fluorescence and phosphorescence, may be employed for sensing by exciting a sample and directly looking for the PL spectrum of the analyte or by indirectly observing changes in the PL of another species affected by the analyte. Optical enzymatic biosensors typically use an indirect mechanism whereby the products of the reaction modify the PL efficiency of nearby dye molecules. For example, conversion of toluene by a monooxygenase consumes dissolved oxygen in the proximity of an oxygen-sensitive ruthenium-based dye thereby altering the dye's PL efficiency and lifetime. Higher analyte levels result in higher reaction rates and thus depleted oxygen levels, reducing oxygen alters phosphorescent emission of the ruthenium dye under constant excitation power.

Each chemosensor or biosensor typically has an optode for coupling light to and from optical fibers to a sensor component. Chemosensors of particular interest herein are biosensors in that they incorporate a biological component in the sensor component. The biological component may be prepared of living organisms embedded in other materials, or may be made of isolated enzymes and/or antibodies combined with other materials.

Many prior sensors have a one-to-one relationship between the electro-optical component and the chemosensor component. These prior sensors typically have an interrogation light source coupled directly or through an optical fiber to the chemosensor component, and an electro-optical detector component coupled directly or through an optical fiber to the chemosensor component.

For example, consider the prior-art sensing device 100 illustrated in FIG. 1; this device has a chemosensor element 102, such as those known in the art or described in the '140 application that undergoes a change in fluorescent properties with analyte concentrations in its environment. A stimulus light source 104 provides light at a stimulus wavelength suitable for stimulating fluorescence in chemosensor element 102. Stimulus light source 104 may be a laser, may be a light-emitting diode, or may be another light source as known in the art. Light from light source 104 passes to chemosensor element 102, and stimulates fluorescent light emissions at a fluorescence wavelength that is typically longer than the stimulus wavelength. In embodiments where light source 104 emits significant light at the fluorescence wavelength, a wavelength-selective device 106, such as a high-pass optical filter, is interposed between light source 104 and chemosensor element 102 to block light at the fluorescence wavelength.

In this device, fluorescent light emitted by chemosensor element 102 passes through a second wavelength-selective device 108, typically a filter, that blocks light at the stimulus wavelength while passing light at the fluorescence wavelength. Light passed by wavelength-selective device 108 enters a photodetector 110. A processing device 112 uses photodetector 110 to make readings of light at the fluorescent wavelength, applies any necessary correction factors, and provides readings of analyte concentrations.

Many chemosensor elements 102 known in the art provide faint fluorescent light at some analyte levels of interest, in part because analyte levels of interest may be quite low. For example, it is desirable to detect substances such as the highly toxic organophosphate Sarin at levels that are below those that cause harm to most mammals. In order to accurately measure such faint fluorescent light, sensitive photodetectors 110 may be required, including such photodetectors as avalanche photodiodes and photomultiplier tubes. Such sensitive photodetectors may be rather costly.

SUMMARY

A measurement system for use with fluorescent chemosensors has multiple stimulus light sources each coupled to at least one sensor. Multiple sensors each receiving light from a different light source connect to each of one or more photodetectors. A processing device provides for driving the light sources in a time-division multiplexed manner, and reads the photodetector at an appropriate time for each sensor. The processing device calibrates the sensor readings and provides them in a way that is identified to the associated sensor.

A measurement system has stimulus light sources and sensors coupled in pairs by a stimulus optical fiber. Each sensor has an optode coupled to a photoluminescent chemosensor component for emitting fluorescent light at a fluorescent wavelength when illuminated by light at the stimulus wavelength. The sensor provides emitted fluorescent light dependent upon an analyte concentration. Multiple chemosensors are coupled to a common photodetector to measure the emitted fluorescent light by sensing optical fibers. A portion up to all of the stimulus and sensing optical fibers may be combined in a single fiber connected to a stimulus light source and photodetector by a 2×2 fiber coupler, bifurcated fiber assembly, dichroic filter, or other optical device for combining two optical paths that may be at different wavelengths. A processing device is provided for analyzing the emitted fluorescent light and controlling the light sources.

A method of monitoring a level of an analyte has a cycle of providing light to a first sensor from a first stimulus light source at a stimulus wavelength; measuring light at a fluorescent wavelength from the first sensor with a photodetector; turning off the first stimulus light source; providing light to a second sensor from a second stimulus light source at the stimulus wavelength; and measuring light at the fluorescent wavelength from the second sensor with the photodetector. In this method, each sensor has an optode coupled to a photoluminescent chemosensor component for emitting fluorescent light at a fluorescent wavelength when illuminated by light at the stimulus wavelength, the emitted fluorescent light being dependent upon an analyte concentration.

BRIEF DESCRIPTION OF THE DRAWINGS

FIG. 1 is a block diagram of a prior art sensing device.

FIG. 2 is a block diagram of an embodiment of a multiplexed system having multiple sensing devices.

DETAILED DESCRIPTION OF THE EMBODIMENTS

Figure 3:
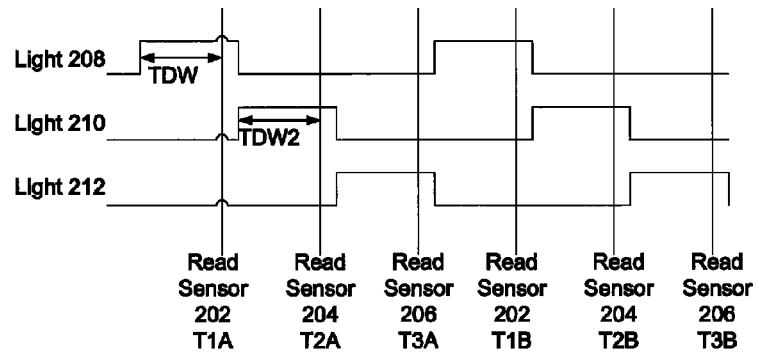
FIG. 3 is a timing diagram of operation of the system of FIG. 2.

Biologically-based photoluminescent chemosensors (biosensors) have been proposed that may be interrogated optically. Each such sensor typically has an optode coupled to a fluorescence chemosensor element. This interrogation is performed by providing stimulus light through the optode and observing returned light through the optode at one or more fluorescent wavelengths, light at fluorescent wavelengths may be emitted by either fluorescence or phosphorescence in the associated chemosensor element. These sensors include sensors having one or more biocomponents comprising a dehalogenase, a hydrolase, a lyase and/or an oxygenase enzyme immobilized and/or stabilized in the sensor. These biosensors may monitor or detect the presence and/or concentration of one or more analytes, such as hydrocarbons and alcohols, polycyclic hydrocarbons, s-triazines, chlorinated ethenes, orthosulfates, organophosphates, or amine-substituted chemicals; this is not intended to be a complete list. S-triazines include, for example, the chlorinated herbicide atrazine, simazine, terbutylazine, propazine, cyanazine, diethylatrazine and deisopropylatrazine, plus other s-triazines, melamine, lindane and DDT. Chlorinated ethenes include, for example, tetrachloroethene (a.k.a., perchloroethene (PCE)), trichloroethene (TCE), dichloroethene isomers and vinyl chloride (VC). Organophosphates include, for example, the pesticides methyl parathion, chlorpyrifos, and diazinon; the nerve agent sarin; and solvents and plasticizers such as tributylphosphate, tris(2-ethylhexyl)phosphate and triphenyl phosphate. Organosulfates include, for example, cerebroside-3-sulfate, phenol sulfates, chondroitin sulfate, karatan sulfate, dermatan sulfate, choline sulfate, polysulfates of cellulose, heparitin sulfate, heparan sulfate, and heparin. Amine-substituted chemicals include, for example, melamine, ammeline, ammelide, serine, biotin, and aniline. There are many other such chemicals that may be of interest.

Enzyme-based biosensors have been developed for ethanol that use alcohol oxidase, which catalyzes the reaction of ethanol and oxygen to form acetaldehyde and hydrogen peroxide. Mitsubayashi et al. described an optical biosensor in which alcohol oxidase was immobilized on the tip of a fiber optic oxygen sensor that used a photoluminescent ruthenium complex. This biosensor was found to detect ethanol in aqueous solutions in the range 0.5-9 millimolar, and was also effective in gaseous samples with ethanol concentrations from 0.7 to 50 ppm. Other researchers used coimmobilized alcohol oxidase and horseradish peroxidase, immobilized on an optical oxygen sensor, to measure methanol in n-hexane in the range 2-90 millimolar.

In addition to chemosensor elements based on enzymatic oxidation with measurement of oxygen consumption as described in the background, other biologically based, optically-read, chemosensor components may incorporate a culture of living microorganisms to provide cofactors such as NADH or to permit detection based on gene expression. Although these sensors require frequent servicing to maintain or replace the cultures, and are a bit slower to react, such biosensors may be prepared for the detection of many hydrocarbons. Detection of various aromatic compounds at approximately 1 millimolar was achieved by Thavarungkul et al. using a culture of *Pseudomonas cepacia*, Rella et al. used *Bacillus stearothermophilus* in a hydroxyethyl methacrylate membrane to measure phenol, catechol, and related compounds. Optically-read biosensors for the measurement of toluene using whole cells expressing toluene o-monooxygenase have resolved 0.3 milligrams per liter. An enzyme-based biosensor embodying a layer containing living cells and other components as an chemosensor element has been demonstrated for dichloroethane in water, as well as atrazine, lindane, and chlorohexane. It has been proposed that such sensors could be lyophilized for storage, and rehydrated before use.

Antibodies to particular analytes have also been used to bind photoluminescent analytes at sensor tips. Chemosensor elements embodying such antibodies may also be used in the system as herein described.

Fluorescent reagents that may be embodied in a biological or non-biological chemosensor include trisodium 8-hydroxy-1,3,6-trisulphonate for pH sensors, fluoro (8-anilino-1-naphthalene sulphonate) for $Na^+$ ion sensors, and acridinium- and quinidinium-based reagents for halide sensors.

A system 200 (FIG. 2) using one or more sensors has several chemosensor components 202, 204, 206, each of which is suitable for monitoring or detecting one or more analytes of interest and which provides fluorescence that varies with the analyte concentration.

Each of these sensor elements is coupled to receive stimulus light from a separate interrogation light source 208, 210, 212, coupled directly or through a stimulus optical fiber to chemosensor component 202, 204, 206. For simplicity, any wavelength-selective devices necessary to exclude light at fluorescence wavelength are not shown separately in FIG. 2 and are presumed to be included in the light source 208, 210, 212 although in an alternative embodiment multiple light sources 208, 210, 212 may exclude light at fluorescent wavelength by using separate light paths through a single wavelength-selective device. Interrogation light source 208, 210, 212 incorporates a light emitting device, which in an embodiment is a pulsed or modulated laser, and in an alternate embodiment is a pulsed or modulated light emitting diode.

Each sensor element 202, 204, 206 is coupled to pass emitted fluorescent light through a sensing optical fiber to a common wavelength-selective device 214, which may be a filter. Light passing through wavelength-selective device 214 continues to a common photodetector 216. Photodetector 216 in an embodiment comprises a photomultiplier tube, in an alternate embodiment photodetector 216 is based on a P-Intrisic-N (PIN) diode. In other embodiments photodetector 216 is based on such other photodetector as is appropriate for detecting light of the fluorescent wavelength. In an alternate embodiment fluorescent from sensor elements 202, 204, 206 is coupled to a wavelength selective device 214 along separate optical paths or separate optical fibers and corresponding separate optical paths emerging from wavelength selective device 214 to converge on a photodetector 216.

Light sources 208, 210, 212 operate independently under control of a processing device 218, which may be a computer or may be a microcontroller such as a Microchip PIC-16, a Motorola 6811, or an Intel 8096 or 8051 family member such as are equipped with an analog-to-digital converter, or may readily communicate with an analog-to-digital converter.

The connections of optical fibers carrying emitted fluorescent light to wavelength-selective device 214 are arranged such that light at stimulus wavelength is substantially unable to pass from one fiber into another.

During operation, system 200 operates according to a time division multiplexing scheme as illustrated in FIG. 3. A repeated cycle occurs in which a first of the light sources 208 is activated by processing device 218 for a dwell time TDW to stimulate fluorescence in a first of the sensors 202. After the dwell time, the processing device uses photodetector 216 to measure light at fluorescent wavelength; this light is received primarily from the first sensor 202 and is measured as R202 in following equations. Next, first light source 208 is turned off and a second of the light sources 210 is activated by processing device 218 for dwell time TDW2 to stimulate fluorescence in a second of the sensors 204. In embodiments where each sensor is of the same type, each dwell time TDW, TDW2 is the same, where sensors have different decay times the dwell times TDW, TDW2 may be determined as appropriate to allow decay of fluorescence in the preceding sensor and adequate stimulation time for a reading. After the dwell time, the processing device uses photodetector 216 to measure light at fluorescent wavelength; this light is received primarily from second sensor 204 and is measured as R204 in the following equations. Next, the second light source 210 is turned off and a third of the light sources 212 is activated by processing device 218 for the dwell time to stimulate fluorescence in a third of the sensors 206. After the dwell time, the processing device uses its analog-to-digital converter and photodetector 216 to measure light at fluorescent wavelength; this light is received primarily from the third sensor 206, and is measured as R206 in following equations, and the third light source 212 is turned off. After any other light sources and detectors are driven, the cycle repeats. Light sources, for example 208 and 210, may overlap briefly when transitioning from one light source to the next light source if convenient and primarily one light source is on when the corresponding sensor is read.

After each measurement of light at stimulus wavelength, processing device 218 applies calibration and correction factors from calibration tables 220 and in an embodiment provides calibrated sensor data to a host system. In an alternative embodiment, processing device 218 compares calibrated sensor data to detection thresholds and activates appropriate warning devices (not shown).

While the system has been illustrated with three sources and three sensors, in principle any number greater than or equal to two each of sources and sensors may be used.

In an embodiment, all sensors are identical and monitor the same analyte at different locations. Since optical fibers, such as fibers 222, 224, are available with low attenuation, and minor attenuation can be adjusted for in calibration tables 220 (FIG. 2), sensors such as sensor 204 may be located one hundred or more meters from remaining components, such as photodetector 216, of the system; this permits monitoring multiple locations within the same industrial plant, or contaminated site undergoing environmental remediation, using a common photodetector 216 and processing device 218.

In an alternative embodiment, each sensor 202, 204, 206 is sensitive to a different analyte, permitting use of a common photodetector 216 to continuously measure contamination by several different analytes. For example, system 200 may monitor a sewage treatment plant or a water treatment plant for several different substances in source water.

Figure 4:
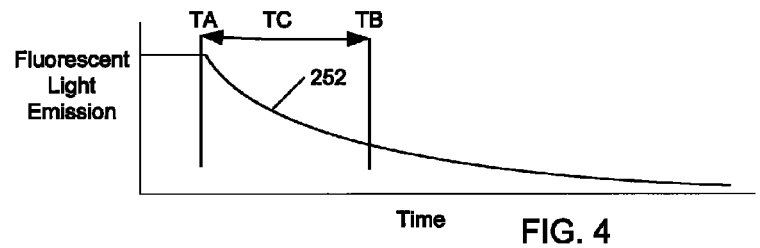
FIG. 4 illustrates decay with time of fluorescence from a sensor.

Many fluorescent materials, including those in sensors as herein described, have an afterglow 252 as illustrated in FIG. 4. The intensity of light emitted at fluorescent wavelength decays with time after the stimulus source is turned off (e.g. at TA), typically following a decay curve that can be expressed as the sum of one or more exponential decay curves. In an embodiment, the difference between times TA and TB is a time constant TC of a predominant component of the decay curve.

In a slow embodiment sensors have a short TC compared to dwell time TDW. In this embodiment, TDW is chosen to be a large enough multiple of time constant TC to prevent undue interference between sensor readings.

In a high speed embodiment, each sensor reading is corrected according to a known decay curve of the sensor or sensors last measured before it in the time-division multiplexing scheme. For example, in a system operating according to the cycle described above with reference to FIG. 3, the corrections are performed as:

Corrected 202 reading=$R202-K1(206)*R206-K2(204)*R204$

Corrected 204 reading=$R204-K1(202)*R202-K2(206)*R206$

Corrected 206 reading=$R206-K1(204)*R204-K2(202)*R202$

Figure 5:
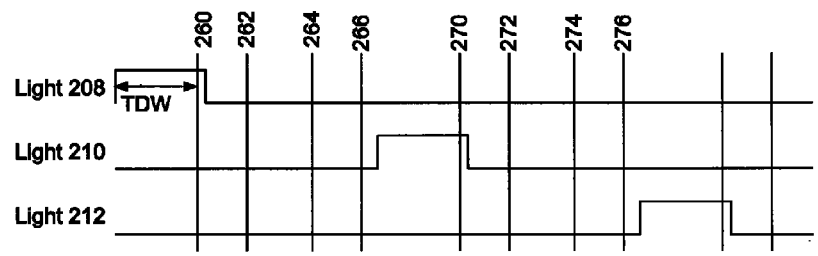
FIG. 5 illustrates measurements of decay time of fluorescence for determining a sensor reading.

In an alternative embodiment, as illustrated in FIG. 5, a stimulus light, such as light 208, is turned on for a dwell time TDW, and light at fluorescent wavelength is measured at time 260 immediately prior to turnoff. In this embodiment, decay time is measured by measuring light received by photodetector 216 at fluorescent wavelength at several decay sampling times 262, 264, 266. In order to prevent crosstalk, in a version of this embodiment a delay of several time constants is allowed before turning on stimulus light 210 coupled to the next sensor to be read in sequence within the cycle. The decrease in light received by photodetector 216 at times 262, 264, 266, and the magnitude of the steady-state photoluminescence at time 260 are used to determine decay rate of the fluorescence. This decay rate is then used to compute a measurement of analyte concentration present at the sensor. In another embodiment, reading immediately prior to turn off 260, 270, is omitted and decay rate is determined only from readings at times 262, 264, 266 taken within several time constants after the stimulus light is turned off.

In an alternative embodiment, once decaying fluorescent light at sufficient sample times 262, 264, 266 is measured to compute the decay rate of the fluorescence, stimulus light 210 coupled to the next sensor to be read in sequence within the cycle is activated. The decay rate of fluorescence from the first sensor 202 is extrapolated to provide values for removing crosstalk by subtracting decaying fluorescence from sensor 202 from samples taken at times 270, 272, 274, 276 and containing information primarily from sensor 204.

In an alternative embodiment, wavelength selective device 214 is a prism or diffraction grating, and photodetector 216 has an array of two or more photosensitive elements. In this embodiment, photodetector 216 provides information regarding spectra of light received from each sensor.

Figure 6:
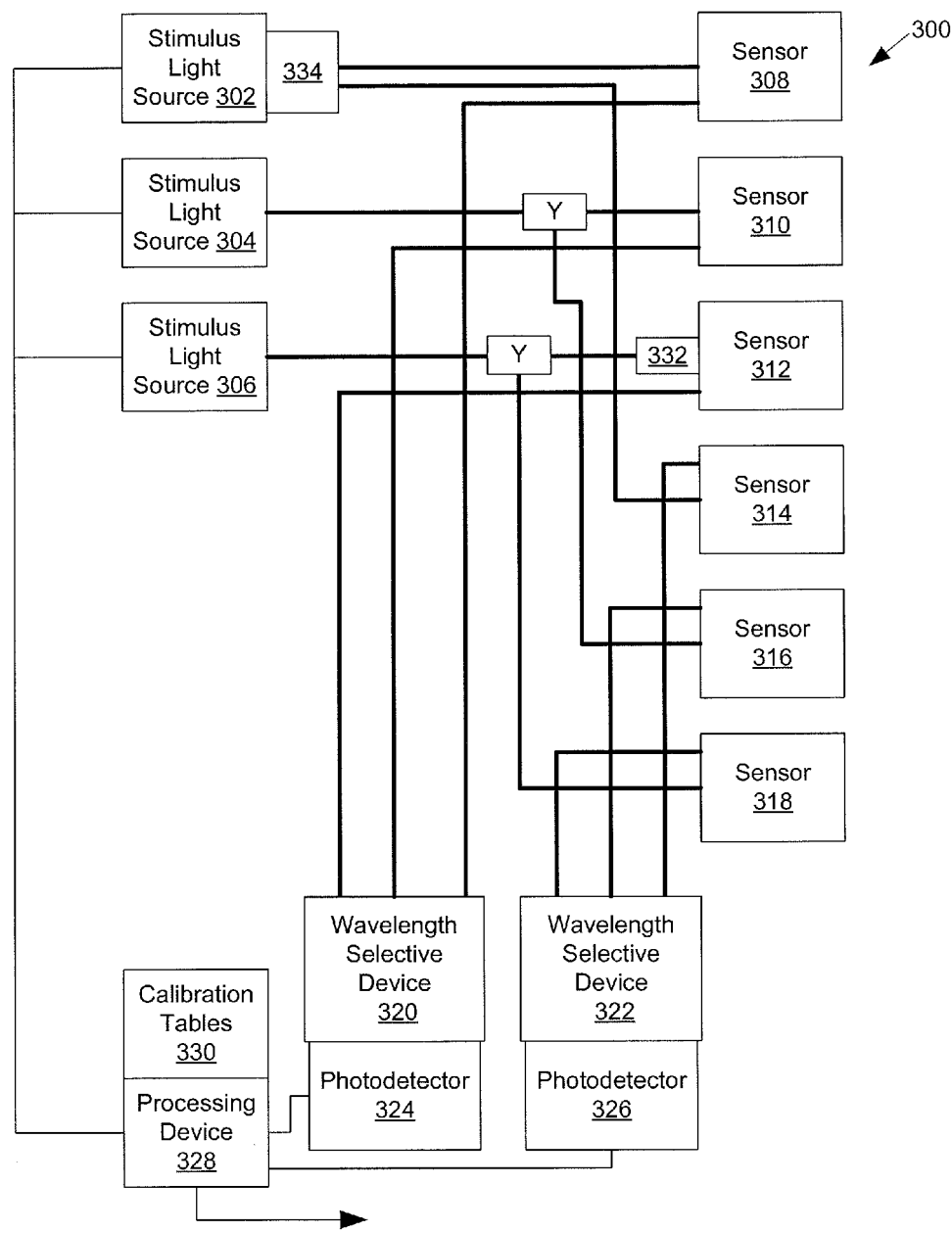
FIG. 6 is a block diagram illustrating an embodiment of an expanded multiplexed system having multiple sensor groups.

In an alternative embodiment, as illustrated in FIG. 6, each stimulus light source 302, 304, 306 couples through stimulus optical fibers to not one, but two, chemosensors 308, 310, 312, 314, 316, 318. In this embodiment, as in the embodiment of FIG. 2, multiple chemosensors couple through sensing optical fibers through each wavelength selective device 320, 322. Each wavelength selective device 320, 322, couples to a photodetector 324, 326. In this embodiment, as in the embodiment of FIG. 2, each chemosensor receives light from only one of the light sources 302, 304, 306, and each chemosensor, such as chemosensor 308, couples to only one wavelength selective device 320, 322. Sensors coupling to the first wavelength selective device 320 are referenced as those of a first sensor group, and sensors coupling to the second selective device 322 are referred to as those of a second sensor group.

In order to prevent crosstalk between sensors of the first sensor group and sensors of the second sensor group, a fluorescence-wavelength blocking device 332, such as an optical filter, is provided at a stimulus-fiber connection of each optode, for preventing emitted light from passing through stimulus-fibers into other sensors and being picked up by their sensing optical fibers.

In an alternative embodiment, a wavelength-selective device such as wavelength selective device 334, which may be a filter, having a single input from the associated light source 302 and multiple outputs connected through separate stimulus fibers to each associated chemosensor 308, 314, serves to permit stimulus wavelength light to enter each stimulus fiber while blocking light, including crosstalk light, at fluorescent wavelength.

In all embodiments, processing device 328, 218, provides calibrated sensor readings derived from reading the biosensors or chemosensors to a host, or compares readings against warning limits and activates warning devices, in a manner such that each sensor reading is clearly identified to the associated sensor.

It is anticipated that the system as herein described, when equipped with appropriate chemosensor elements, is of use as an environmental monitoring system in the following fields:

Water treatment process monitoring. In both drinking water and wastewater treatment processes it is desirable to monitor contaminant levels for the protection of human and environmental health. Given the high flow rates of these processes, continuous monitoring of specific chemicals is desirable.

Protection from chemical terrorism of water supplies. The possibility of terrorist attacks by the addition of toxic chemicals to water supplies has arisen in recent years. Devices capable of continuous monitoring for multiple toxic analytes at low levels are of particular interest to detect such chemicals.

Monitoring of remediation processes. Once a remediation process has been designed and implemented at a contaminated site, its effectiveness must be established through a program of periodic monitoring, often at more than one location on the site. Such monitoring can be performed with a monitoring system as herein described.

Environmental monitoring. It is often desirable to monitor sensitive water sources (ground water wells, rivers, lakes, etc.) that are downgradient from industrial sites and other sources of contaminants that may leak or spill.

Precision agriculture. The goal of precision agriculture is to apply the correct amount of fertilizer and pesticide on every portion of a field, recognizing that different amounts are required depending on slope, exposure, soil type, and other factors. Multiple chemosensors may be implanted in a field and coupled by optical fiber to a common photodetector at a central monitoring point in the field.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system and reasonable variations thereof, which might be said to fall therebetween.

What is claimed is:

1. A measurement system comprising:
a plurality of stimulus light sources that provide stimulus light;
a plurality of sensors each coupled to a light source of the light sources by a stimulus optical fiber, each sensor comprising an optode coupled to a photoluminescent chemosensor component for emitting fluorescent light at a fluorescent wavelength when illuminated by light at the stimulus wavelength, the emitted fluorescent light dependent upon an analyte concentration;
sensing optical fibers coupling each sensor to at least one photodetector to quantify the emitted fluorescent light;
wherein a first and second sensor of the plurality of sensors couple simultaneously to a photodetector of the at least one photodetector;
apparatus for selectively energizing a first and second subset of the light sources and for analyzing the emitted fluorescent light as measured by the at least one photodetector;
wherein the first sensor is coupled to a light source of the first subset of the light sources, and the second sensor is coupled to a light source of the second subset of the light sources;
wherein the measurement system is adapted to provide readings of analyte concentration at the first and second sensor and distinguishes between the first and second sensor by separately energizing the subsets of light sources; and
wherein the measurement system is configured to stimulate and read the first sensor prior to stimulating and reading the second sensor, and wherein the measurement system applies a correction to a reading of the second sensor for afterglow of the first sensor by subtracting from a reading of the second sensor at least a product of a constant multiplied by a reading of the first sensor.

2. The system of claim 1, wherein the photoluminescent chemosensor component is adapted to emit fluorescent light with a decay time dependent upon the analyte concentration.

3. The system of claim 1, wherein the photoluminescent chemosensor component is adapted to emit fluorescent light with an intensity dependent upon the analyte concentration.

4. The system of claim 3 wherein the system is configured to apply a correction to a reading of a third sensor for afterglow of previously stimulated first and second sensors by subtracting from a reading of the third sensor a sum of products of constants multiplied by readings of the first and second sensors.

5. The system of claim 1 wherein each sensor is a biosensor having a biological component.

6. The system of claim 5 wherein at least one sensor comprises extracted enzymes in a matrix.

7. The system of claim 5 wherein at least one sensor comprises living organisms in a matrix.

8. The system of claim 7 wherein a first and a second sensor of the sensors are coupled to a first photodetector of the photodetectors, where the first and second sensors are coupled to separate light sources, and comprising a third sensor coupled the same light source as the first sensor, and wherein the third sensor is coupled to a second photodetector of the photodetectors.

9. The system of claim 1 wherein the sensing optical fibers couple to the at least one photodetector through a common wavelength selective device that blocks light of stimulus wavelength.

10. The system of claim 1 wherein the stimulus optical fibers each couple to the stimulus light sources through a wavelength selective device that blocks light of the fluorescent wavelength.

11. A method of monitoring a level of an analyte comprising performing a cycle comprising the steps:
Providing light to a first sensor from a first stimulus light source;
Measuring light at a fluorescent wavelength from the first sensor with a photodetector;
Turning off the first stimulus light source Providing light to a second sensor from a second stimulus light source at the stimulus wavelength;
Measuring light at the fluorescent wavelength from the second sensor with the photodetector to provide a reading of the second sensor; and
Correcting the reading of the second sensor for afterglow of the first sensor;
Wherein each sensor comprises an optode coupled to a photoluminescent chemosensor component for emitting fluorescent light at a fluorescent wavelength when illuminated by stimulus light, the emitted fluorescent light dependent upon an analyte concentration.

12. The method of claim 11, wherein the emitted fluorescent light from the first sensor has a decay time dependent upon the analyte concentration, and further comprising measuring light at fluorescent wavelength with the photodetector at a plurality of times between the steps of turning off the first stimulus light source and providing light to a second sensor.

13. The method of claim 11, wherein the emitted fluorescent light has an intensity dependent upon the analyte concentration.

14. The method of claim 11 wherein a common wavelength selective device is provided at the photodetector for passing light at the fluorescent wavelength and preventing crosstalk between the first and the second sensor.

15. The method of claim 11 wherein the first and the second stimulus light sources couple to the sensors through a wavelength selective device that blocks light of the fluorescent wavelength.

16. The method of claim 11 wherein each sensor is a bio sensor having a biological component.

17. The system of claim 16 wherein at least one sensor comprises extracted enzymes in a matrix.

18. The system of claim 16 wherein at least one sensor comprises living organisms in a matrix.

19. The system of claim 11 wherein the wavelength of each stimulus light source is the same.

20. A measurement system comprising:
a plurality of stimulus light sources that provide stimulus light;
a plurality of sensors each coupled to a light source of the light sources by a stimulus optical fiber, each sensor comprising an optode coupled to a photoluminescent chemosensor component for emitting fluorescent light at a fluorescent wavelength when illuminated by light at the stimulus wavelength, the sensor configured to emit fluorescent light dependent upon an analyte concentration;
sensing optical fibers coupling each sensor to at least one photodetector to quantify the emitted fluorescent light;
wherein a first and second sensor of the plurality of sensors couple simultaneously to a photodetector of the at least one photodetector through a common filter;
apparatus for selectively energizing a first and second subset of the light sources and for analyzing the emitted fluorescent light as measured by the at least one photodetector;
wherein the first sensor is coupled to a light source of the first subset of the light sources, and the second sensor is coupled to a light source of the second subset of the light sources; and
wherein the measurement system is adapted to provide readings of analyte concentration at the first and second sensor and distinguishes between the first and second sensor by separately energizing the subsets of light sources.

21. The system of claim 20, wherein the photoluminescent chemosensor component is adapted to emit fluorescent light with a decay time dependent upon the analyte concentration.

22. The system of claim 20, wherein the photoluminescent chemosensor component is adapted to emit fluorescent light with an intensity dependent upon the analyte concentration.

23. The system of claim 20 wherein each sensor is a bio sensor having a biological component.

24. The system of claim 23 wherein at least one sensor comprises extracted enzymes in a matrix.

25. The system of claim 23 wherein at least one sensor comprises living organisms in a matrix.

26. The system of claim 20 wherein the stimulus optical fibers each couple to the stimulus light sources through a wavelength selective device that blocks light of the fluorescent wavelength.

* * * * *